United States Patent
Scheer et al.

(10) Patent No.: US 6,767,442 B1
(45) Date of Patent: Jul. 27, 2004

(54) SENSOR ELEMENT FOR DETERMINING THE OXYGEN CONCENTRATION IN GAS MIXTURES AND METHOD FOR ITS MANUFACTURE

(75) Inventors: Heiner Scheer, Berghuelen (DE); Udo Jauernig, Yokohama (JP); Hans-J erg Renz, Leinfelden (DE); Lothar Diehl, Stuttgart (DE); Dieter Lindauer, Muehlacker (DE); Juergen Karle, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 78 days.

(21) Appl. No.: 09/830,825
(22) PCT Filed: Aug. 23, 2000
(86) PCT No.: PCT/DE00/02879
  § 371 (c)(1),
  (2), (4) Date: Jul. 30, 2001
(87) PCT Pub. No.: WO01/16588
  PCT Pub. Date: Mar. 8, 2001

(30) Foreign Application Priority Data

Aug. 28, 1999 (DE) .......................................... 199 41 051

(51) Int. Cl.$^7$ ........................ G01N 27/409; G01N 27/41
(52) U.S. Cl. ........................ 204/425; 204/426; 204/427
(58) Field of Search ................................. 204/421–429

(56) References Cited

U.S. PATENT DOCUMENTS 3,776,831 A * 12/1973 Roy et al.
4,487,680 A * 12/1984 Logothetis et al.
4,502,939 A * 3/1985 Holfelder et al.
4,505,807 A * 3/1985 Yamada
4,797,194 A * 1/1989 Mase et al.
4,900,425 A * 2/1990 Sasayama et al.
5,298,147 A * 3/1994 Nakae et al.
5,314,604 A * 5/1994 Friese et al.
5,529,677 A * 6/1996 Schneider et al.
5,676,811 A * 10/1997 Makino et al.
6,059,947 A * 5/2000 Kato et al.
6,375,816 B1 * 4/2002 Jach et al.

FOREIGN PATENT DOCUMENTS

DE  195 39 357  8/1996
DE  196 47 144  5/1997
EP  0 678 740  10/1995

* cited by examiner

*Primary Examiner*—Kaj K. Olsen
(74) *Attorney, Agent, or Firm*—Kenyon & Kenyon

(57) ABSTRACT

A sensor element for determining the concentration of gas components in gas mixtures, particularly for determining the oxygen concentration in exhaust gases of internal combustion engines. It contains a pump cell, which pumps oxygen into or out of a measuring gas chamber, as well as a concentration cell, which has a reference electrode situated in the reference gas channel, and has a measuring electrode. The measuring gas chamber and the reference gas channel are situated in the same layer plane of the sensor element, and are separated from each other by a partition, which is produced by applying a ceramic paste to an adjacent, solid electrolyte foil.

18 Claims, 2 Drawing Sheets

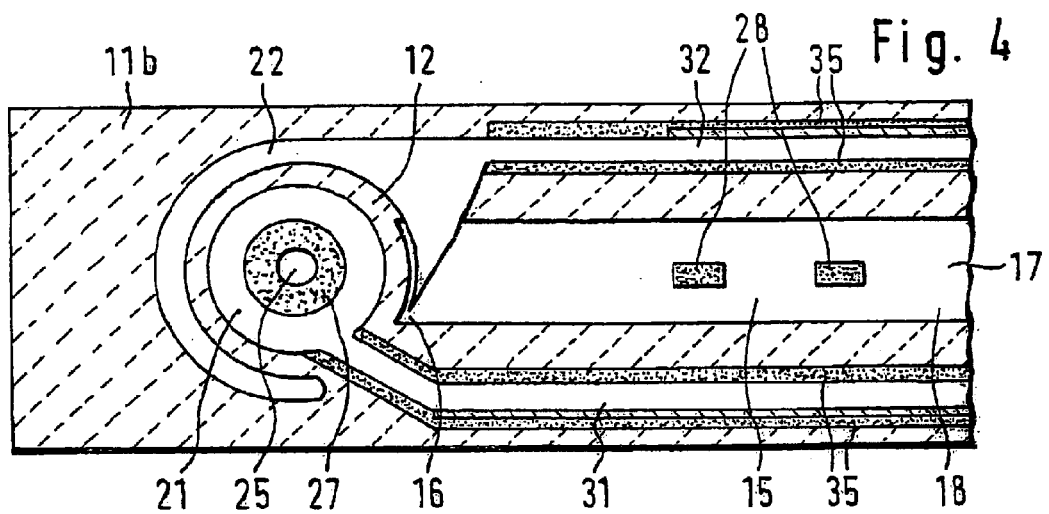
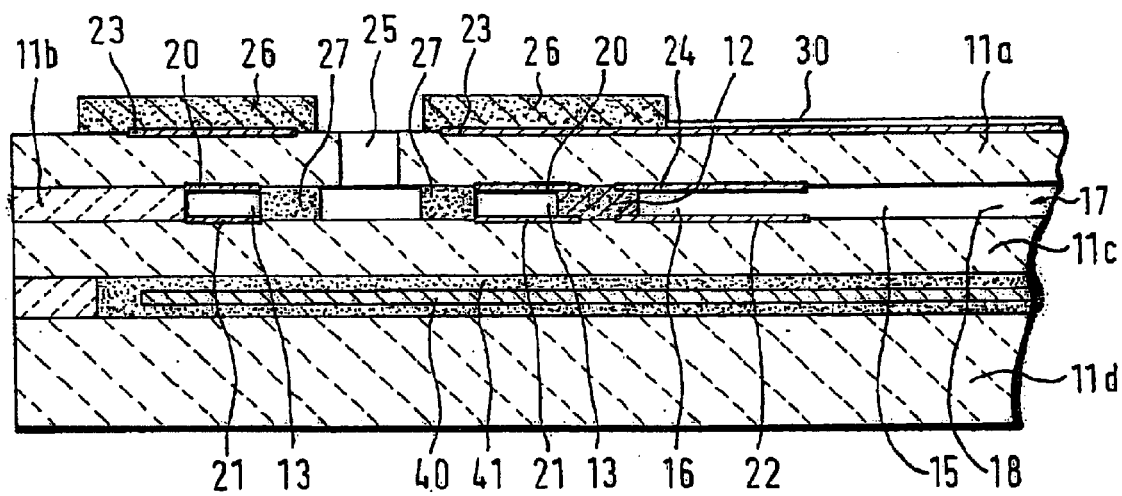
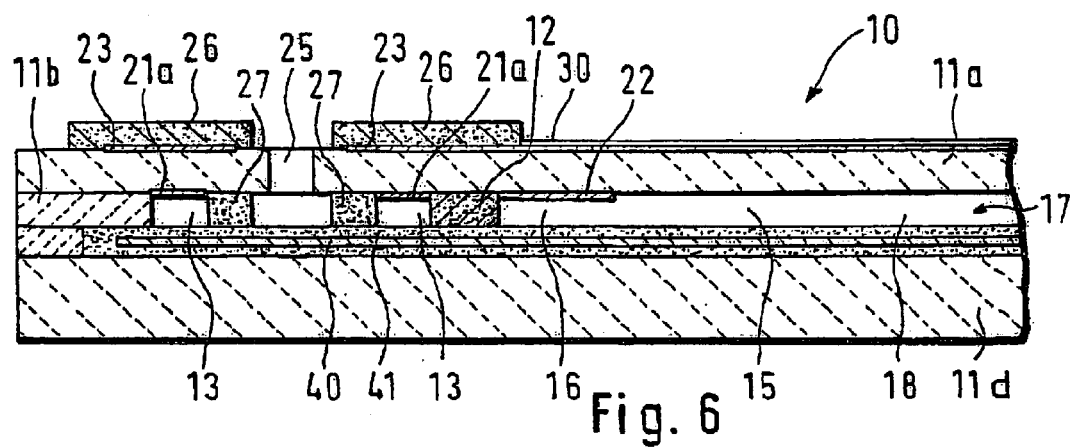

1

SENSOR ELEMENT FOR DETERMINING THE OXYGEN CONCENTRATION IN GAS MIXTURES AND METHOD FOR ITS MANUFACTURE

FIELD OF THE INVENTION

The present invention relates to a sensor element for determining the oxygen concentration in gas mixtures and also relates to a method for manufacturing such sensors.

BACKGROUND INFORMATION

An oxygen sensor, also referred to as a broadband lambda probe, is normally used today for controlling the air-fuel ratio of combustion mixtures for motor vehicle engines. This sensor relies on the interaction of an electrochemical pump cell and a concentration cell. With the aid of the electrodes of the pump cell, oxygen is pumped from a measuring gas chamber of the sensor into the exhaust gas stream, or from the exhaust gas stream into the measuring gas chamber. To this end, one of the pump electrodes is deposited in the measuring gas chamber, and one is deposited on the outer surface of the sensor element and exposed to the exhaust gas stream. The electrodes of the concentration cell are arranged so that one is situated in the measuring gas chamber, but the other is situated with the in a reference gas channel normally filled with air. This arrangement allows the oxygen potential of the measuring electrode in the measuring gas chamber to be compared with the reference oxygen potential of the reference electrode, in the form of a measurable voltage applied at the concentration cell. With regard to measuring technique, the pump voltage to be applied at the electrodes of the pump cell is selected so as to maintain a predetermined voltage value at the concentration cell. The pump current flowing between the electrodes of the pump cell is utilized as a test signal proportional to the oxygen concentration.

The measuring gas chamber and the reference gas channel are usually positioned in different planes of the sensor element, so that the reference gas channel is located underneath the measuring gas chamber. However, this requires at least one additional, solid electrolyte layer, which contains the reference gas channel. German Patent Application No. 196 47 144 describes, at least as a variant, an element for measuring the air-fuel ratio, where the reference gas channel is situated in the same layer plane as the measuring gas chamber. However, in the case of such a layer, experience shows that a minimum layer thickness is dependent on stamping processes during manufacture. In addition, the modified arrangement of the gas chambers creates problems relating to measuring technique, since such an arrangement increases the internal resistance of the concentration cell, and results in a one-sided loading of the measuring and reference electrodes.

SUMMARY OF THE INVENTION

The sensor element and method according to the present invention, respectively, have the advantage that the layer thickness of the layer containing both the measuring gas chamber and the reference gas channel can be varied. A layer that has a very low layer thickness, or a layer having very filagree-like boundaries of the gas chambers contained therein, and having supporting elements not connected to the boundaries may be attained.

The effect of adapting the partition situated between the measuring gas chamber and the reference gas channel on the geometry of the measuring electrode situated in the measuring gas chamber, is such that only small clearance exists between the measuring gas chamber and the reference gas channel. Therefore, the internal resistance of the sensor-element concentration cell is decreased. Furthermore, it is advatageous to design the reference electrode, located in the reference gas channel, in such a manner that it adapt to the geometry of the partion between the measuring gas amber and the reference gas channel. Also the surface of the reference electrode facing in the direction of the partition is as large as possible. This permits a uniform loading of the entire electrode surface, and decreases the electrical resistance of the concentration cell that is made of the measuring electrode and the reference electrode. This is achieved in an advantageous manner when the measuring electrode is circular and the reference electrode is led around the measuring gas chamber, which is circular as well. In addition, the internal resistance of this sensor element's concentration cell exhibits an easily-evaluated temperature dependence, which can be used to control the temperature of the sensor element.

In another exemplary embodiment, the measuring and pump electrodes, which are usually arranged separately in the measuring gas chamber, are advantageously combined into one electrode. This allows one layer plane to be dispensed with, and further simplifies the sensor design.

By appropriately designing the layer assembly, the resistance heater intended for the sensor element into the sensor element can be incorporated so that the resistance heater is equidistant from the two large surfaces of the sensor element. This results in low mechanical stresses especially on the heater-side edges of the sensor element during the heating phase and during operation.

BRIEF DESCRIPTION OF THE DRAWINGS

FIG. 4 shows a longitudinal section through the sensor element according to a fourth exemplary embodiment.

FIG. 5 shows a cross-section through the large surface of the sensor element according to an exemplary embodiment.

FIG. 6 shows a cross-section through the large surface of the sensor element according to an additional exemplary embodiment.

DETAILED DESCRIPTION

Figure 1:
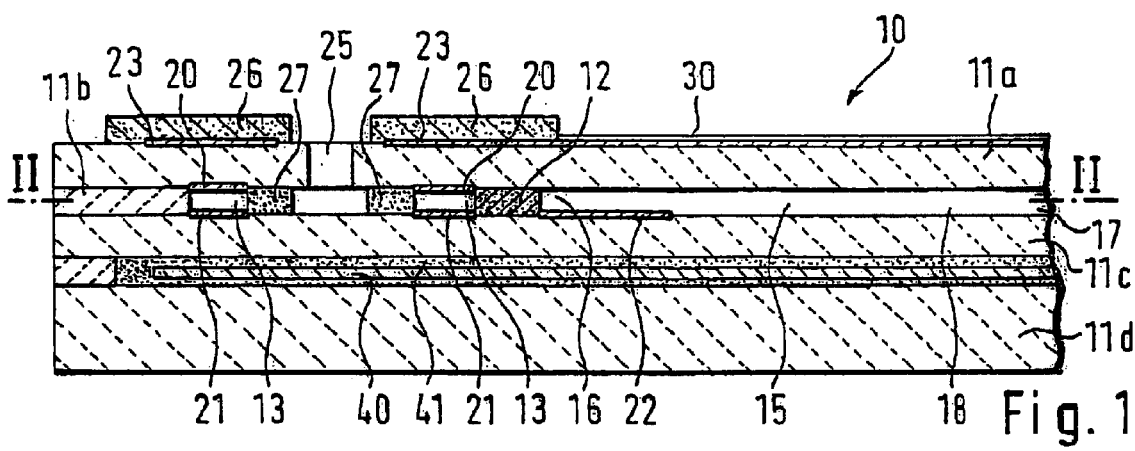
FIG. 1 shows a cross-section through the large surface of the sensor element according to the present invention.
Figure 2:
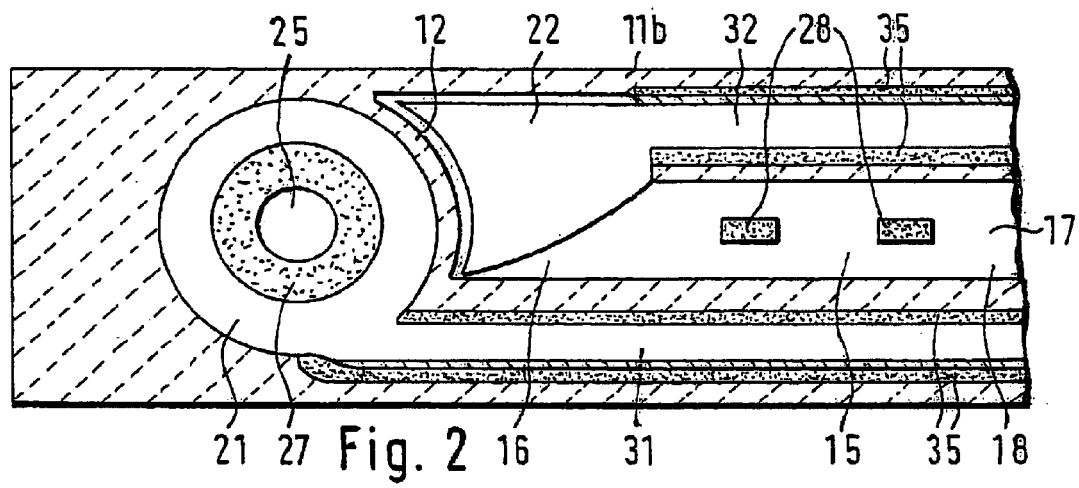
FIG. 2 shows a longitudinal section through the sensor element, along line II—II in FIG. 1.

FIGS. 1 and 2 show a basic design of a first example embodiment according to the present invention. As shown, a planar sensor element 10 of an electrochemical gas sensor has a plurality of solid electrolyte layers, for example, 11a, 11b, 11c, and 11d, that conduct oxygen ions. In this context, solid electrolyte layers 11a, 11c, and 11d are designed as ceramic foils, and form a planar ceramic body. They are made of a solid electrolyte material that conducts oxygen ions, such as $ZrO_2$ stabilized or partially stabilized by $Y_3O_3$.

In contrast, solid electrolyte layer 11b is produced by screen-printing a pasty ceramic material, e.g., on solid electrolyte layer 11a. The solid electrolyte material used as a ceramic component of the pasty material may be the same as the one which makes up solid electrolyte layers 11a, 11c, and 11d.

The integrated form of the planar ceramic body of sensor element 10 is produced in a conventional manner, by laminating together the ceramic foils printed over with solid electrolyte layer 11b and functional layers, and by subsequently sintering the laminated structure.

Sensor element 10 contains two gas chambers, a measuring gas chamber 13 and a reference gas channel 15. These are situated in the same layer plane, e.g., 11b, and separated from each other in a gas-tight manner, by a partition 12. Reference gas channel 15 is put in contact with a reference gas atmosphere, by a gas intake 17 whose one end leads out of the planar body of sensor element 10. It has an end 16 on the side of the measuring gas chamber, and an end 18 on the side of the gas intake. Supporting elements 28 are integrated in the middle of reference gas channel 15, along a longitudinal axis of the sensor element. These permit the reference gas channel to have a wide design, without decreasing the rigidity of the sensor element. As an alternative, the reference gas channel can also be at least partially filled in with a porous ceramic material.

For example, measuring gas chamber 13 is designed to be circular, and is connected to the gas-mixture atmosphere by opening 25. Opening 25 is situated in solid electrolyte layer 11a, normal to the surface of sensor element 10.

An outer pump electrode 23, which can be covered by a porous protective layer 26, and can be arranged so as to encircle opening 25, is positioned on the large surface of sensor element 10 directly facing the measuring gas, on solid electrolyte layer 11a. Situated on the side of solid electrolyte layer 11a that faces the measuring gas chamber is corresponding inner pump electrode 20, which is designed to be circular as well, so as to be adapted to the circular geometry of measuring gas chamber 13. Together, the two pump electrodes form a pump cell.

In measuring gas chamber 13, a measuring electrode 21 is located opposite to inner pump electrode 20. This measuring electrode may also have a circular design. Corresponding reference electrode 22 is situated in reference gas channel 15. In this context, the reference electrode can be formed on the side of reference gas channel 15 that points in the direction of the large surface of the sensor element exposed to the gas-mixture atmosphere, or the reference electrode can also be formed on the side of reference gas channel 15 that is opposite to the large surface of the sensor element exposed to the gas-mixture atmosphere. Measuring and reference electrodes 21, 22 form a Nernst or concentration cell together.

A porous diffusion barrier 27 is arranged inside measuring gas chamber 13, in front of inner pump electrode 20 and measuring electrode 21, in the diffusion direction of the measuring gas. Porous diffusion barrier 27 constitutes a diffusion resistor with regard to the gas diffusing towards electrodes 20, 21. In the case of a reference gas channel 15 filled with a porous ceramic material, diffusion barrier 27 and the filling of reference gas channel 15 may be made of the same material, in order to efficiently manufacture them in one method step.

Outer pump electrode 23 is contacted by a printed circuit trace 30, which is deposited on the surface of solid electrolyte layer 11a. Measuring electrode 21 and reference fit electrode 22 are contacted by printed circuit traces 31, 32, which are led between solid electrolyte layers 11b and 11c, and are connected to the large surface of the sensor element by plated-through holes not shown. All of the printed circuit traces are insulated from the solid electrolyte layers by insulation 35, which, for example, can be made of $Al_2O_3$.

In order to ensure that the measuring gas components are brought into thermodynamic equilibrium at the electrodes, all of the electrodes used are made of a catalytically active material, such as platinum, the electrode material for all of the electrodes being applied as cermet in a conventional manner, in order to sinter the electrode material to the ceramic foils.

In addition, a resistance heater 40 is situated between solid electrolyte layers 11c and 11d, and is embedded in electrical insulation 41, e.g., made of $Al_2O_3$. Sensor element 10 is heated to the appropriate operating temperature of, e.g., 750° C., by resistance heater 40.

Together, inner and outer pump electrodes 20, 23 form a pump cell. This transports oxygen out of and into measuring gas chamber 13. Measuring electrode 21 and reference electrode 22 are interconnected as a concentration cell. This allows the oxygen potential of measuring electrode 21, which is a function of the oxygen concentration in measuring gas chamber 13, to be directly compared to the constant oxygen potential of reference electrode 22, in the form of a measurable electrical voltage. The level of the pump voltage to be applied to the pump cell is selected in such a manner, that a constant voltage, e.g., 450 mV, exists at the concentration cell. The pump current flowing between the electrodes of the pump cell is utilized as a measuring signal proportional to the oxygen concentration in the exhaust gas.

As discussed above, the problem with this overall arrangement is that the parallel arrangement of the gas chambers markedly increases the internal resistance of the concentration cell. This is caused by the longer path that the charge carriers must cover inside the solid electrolyte. For this reason, measuring and reference electrodes 21, 22 are spatially arranged to be as close as possible to each other. This is primarily rendered possible by the screen-printing technique used in manufacturing the sensor element, since, in this manner, partition 12 can be designed to be very thin. The relatively short distance of the two electrodes from each other results in an internal resistance of the concentration cell which is only slightly greater than conventional sensors, and can be used to regulate the temperature of the sensor element.

The sharply one-sided loading of the measuring and reference electrodes, in comparison with conventional types of sensors having the gas chambers arranged one over another, represents an additional problem. Since the charge carriers inside the solid electrolyte prefer the shortest path between the two electrodes, the compartments of measuring and reference electrodes 21, 22 facing the other respective electrode are the most highly loaded. This fact is particularly taken into account by adapting the geometry of reference gas channel 15 and reference electrode 22. Along these lines, reference electrode 22 is designed in such a manner that its top surface reaches its maximum dimension at the end of reference channel 15 on the side of the measuring gas, so that the center of mass of the electrode surface is shifted as closely as possible to the center point of measuring electrode 21.

Figure 3:
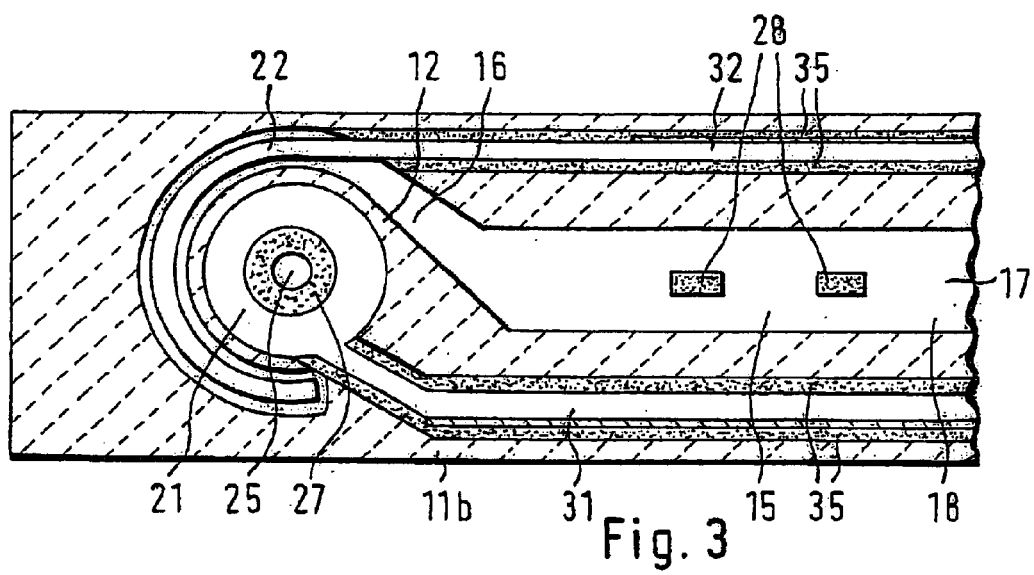
FIG. 3 shows a longitudinal section through the sensor element according to a third exemplary embodiment.

A second exemplary embodiment is represented in FIG. 3. In this exemplary embodiment, both reference gas channel 15 and reference electrode 22 are led around measuring gas chamber 13. In this manner, the two form a segment of a circular ring. This enlarges the compartment of reference electrode 22 on the measuring-gas side, and reduces the load on the electrode. In the d.c. operation used to control the pump voltage, the reference electrode is in direct contact with the reference gas atmosphere. However, the sensor-element temperature control, which is based on determining the internal resistance of the Nernst cell, can also be implemented using a.c. voltage. In this case, the contact with the reference gas atmosphere is not required. Therefore, it is sufficient when only a part of the reference-electrode surface is directly exposed to the reference gas atmosphere. This allows the sensor design represented in FIG. 3 to be simplified, as shown in FIG. 4. Reference electrode 22 continues to be led around measuring gas chamber 13 in a circular ring segment, but reference gas channel 15 does not.

In addition, the spatial dimensions of measuring electrode 21 are not restricted by the size of measuring gas chamber 13. FIG. 5 depicts a sensor design that includes a measuring electrode 21, whose dimensions extend beyond measuring gas chamber 13, and thus reduce the internal resistance of the Nernst cell. Two reference electrodes 22, 24 are also provided.

An additional exemplary embodiment is represented in FIG. 6. It is possible to combine inner pump electrode 20 and measuring electrode 21 into measuring electrode 21a. If this measuring electrode 21a is situated on the side of solid electrolyte layer 11a that faces the gas chambers, as is also the case with reference electrode 22, then one can dispense with inserting solid electrolyte layer 11c, and the sensor design is simplified further. By selecting an appropriately thick, solid electrolyte layer 11d, it is then possible to integrate heating element 40 into the sensor element in such a manner that it is equidistant from the two large surfaces of the sensor element, and is therefore arranged symmetrically. This sharply reduces the mechanical stresses occurring during the heating phase, above all, at the edges of the sensor element.

The sensor element according to the present invention and the method for manufacturing it are not limited to the specified, practical options for refinement, but rather further specific embodiments are possible which contain one or more solid electrolyte layers produced using a printing method.

What is claimed is:

1. A sensor element for determining a concentration of gas components in gas mixtures, comprising:
    a measuring gas chamber;
    at least one pump cell which pumps oxygen at least one of into and out of the measuring gas chamber;
    at least one concentration cell including at least one reference electrode and a measuring electrode, the at least one reference electrode interacting with the measuring electrode, the measuring gas chamber and the reference gas channel being situated in a same layer plane;
    a reference gas channel, the at least one reference electrode being arranged in the reference gas channel, the reference gas channel providing the at least one reference electrode contact with a reference gas intake; and
    a partition arranged between the measuring gas chamber and the reference gas channel, the partition having a measuring-gas side and a reference-gas side, the partition including a base, the base formed from a ceramic paste applied to an adjacent solid electrolyte foil.

2. The sensor element as recited in claim 1, wherein the sensor element is configured to determine an oxygen concentration in exhaust gases of internal combustion engines.

3. The sensor element as recited in claim 1, wherein a geometry of the partition is adapted to a reference-gas-side boundary of the measuring electrode.

4. The sensor element as recited in claim 1, wherein the reference electrode has a boundary on a side of the measuring gas chamber, the boundary being adapted to a shape of the reference-gas side of the partition.

5. The sensor element as recited in claim 1, wherein the pump cell includes an inner pump electrode arranged in the measuring gas chamber opposite to the measuring electrode.

6. The sensor element as recited in claim 5, further comprising an annular diffusion barrier, the diffusion barrier arranged in front of the measuring electrode and the inner pump electrode in a diffusion direction of the gas mixture, the measuring electrode and the inner pump electrode being annular in design.

7. The sensor element as recited in claim 1, wherein the measuring electrode is situated in the measuring gas chamber and forms an inner pump electrode of the pump cell.

8. The sensor element as recited in claim 1, further comprising:
    a large surface facing the gas mixture, the large surface having at least one opening; and
    wherein the measuring gas chamber is coupled to at least one of the at least one opening on the large surface of the sensor element facing the gas mixture, the opening being substantially normal to an upper surface of the sensor element, the opening allowing the gas mixture to enter into the measuring gas chamber.

9. The sensor element as recited in claim 8, wherein the measuring gas chamber is circular, a center point of the circle lying on a center line of one of the at least one opening.

10. The sensor element as recited in claim 8, wherein the reference electrode is situated on a side of the reference gas channel nearest the large surface of the sensor element exposed to the gas mixture.

11. The sensor element as recited in claim 1, wherein two diametrically opposed reference electrodes are situated in the reference gas channel.

12. The sensor element as recited in claim 1, wherein the measuring electrode includes a portion situated outside of the measuring gas chamber.

13. The sensor element as recited in claim 1, wherein at least one of the at least one reference electrodes includes a portion situated outside of the reference gas channel (15).

14. The sensor element as recited in claim 1, wherein the reference gas channel is at least partially filled in with a porous ceramic material.

15. The sensor element as recited in claim 1, further comprising:
    a first solid electrolyte foil exposed to the gas mixture; and
    a solid electrolyte layer containing the measuring gas chamber and the reference gas channel;
    wherein the solid electrolyte layer is directly deposited on the solid electrolyte foil.

16. The sensor element as recited in claim 15, further comprising:
    a second solid electrolyte foil;
    a third solid electrolyte foil; and
    a heating element arranged between the second and third solid electrolyte foils,
    wherein the third solid electrolyte foil has a thickness dimensioned so that the heating element is approximately equidistant from two large surfaces of the sensor element.

17. A sensor element for determining a concentration of gas components in gas mixtures, comprising:
    a measuring gas chamber;
    at least one pump cell which pumps oxygen at least one of into and out of the measuring gas chamber;
    at least one concentration cell including at least one reference electrode and a measuring electrode, the at least one reference electrode interacting with the measuring electrode, the measuring gas chamber and the reference gas channel being situated in a same layer plane;

a reference gas channel, the at least one reference electrode being arranged in the reference gas channel, the reference gas channel providing the at least one reference electrode contact with a reference gas intake; and a partition arranged between the measuring gas chamber and the reference gas channel, the partition having a measuring-gas side and a reference-gas side, the partition including a base, the base formed from a ceramic paste applied to an adjacent solid electrolyte foil, wherein the reference electrode has a tapered surface, the surface having a first edge toward an end of the reference gas channel nearest the measuring gas chamber and a second edge toward an end of the reference gas channel nearest the reference gas intake, the surface being tapered from the first edge to the second edge, the reference electrode surface approaching a center point of the measuring electrode.

18. A sensor element for determining a concentration of gas components in gas mixtures, comprising:

a measuring gas chamber;

at least one pump cell which pumps oxygen at least one of into and out of the measuring gas chamber;

at least one concentration cell including at least one reference electrode and a measuring electrode, the at least one reference electrode interacting with the measuring electrode, the measuring gas chamber and the reference gas channel being situated in a same layer plane;

a reference gas channel, the at least one reference electrode being arranged in the reference gas channel, the reference gas channel providing the at least one reference electrode contact with a reference gas intake; and a partition arranged between the measuring gas chamber and the reference gas channel, the partition having a measuring-gas side and a reference-gas side, the partition including a base, the base formed from a ceramic paste applied to an adjacent solid electrolyte foil, wherein at least a section of at least one of the reference gas channel and the reference electrode is led around the measuring gas chamber.

* * * * *

UNITED STATES PATENT AND TRADEMARK OFFICE
CERTIFICATE OF CORRECTION

PATENT NO. : 6,767,442 B1
DATED : July 27, 2004
INVENTOR(S) : Heiner Scheer et al.

It is certified that error appears in the above-identified patent and that said Letters Patent is hereby corrected as shown below:

Title page,
Item [75], Inventors, change "Hans-J erg" to -- Hans-Joerg --

Column 2,
Line 7, change "that is adapt" to -- that it adapts --
Line 8, change "the measuring gas amber" to -- the measuring gas chamber --
Line 59, change "stabilized $Y_3O_3$." to -- stabilized $Y_2O_3$. --

Column 5,
Line 57, change "solid electrolyte foil" to -- solid electrolyte --
Line 57, insert -- wherein the measuring electrode has an annular design and is formed in the measuring gas chamber, and the partition is a segment of a circular ring. --

Signed and Sealed this

Thirty-first Day of May, 2005

JON W. DUDAS
*Director of the United States Patent and Trademark Office*